(12) United States Patent
Modarresi

(10) Patent No.: US 10,851,029 B2
(45) Date of Patent: Dec. 1, 2020

(54) FUEL CELL REACTOR AND A PROCESS FOR DIRECT CONVERSION OF A HYDROCARBON-CONTAINING GAS TO A HIGHER HYDROCARBONS PRODUCT

(71) Applicant: Haldor Topsøe A/S, Kgs. Lyngby (DK)

(72) Inventor: Hassan Modarresi, Lyngby (DK)

(73) Assignee: Haldor Topsoe A/S, Lyngby (DK)

( * ) Notice: Subject to any disclaimer, the term of this patent is extended or adjusted under 35 U.S.C. 154(b) by 402 days.

(21) Appl. No.: 15/037,734

(22) PCT Filed: Nov. 4, 2014

(86) PCT No.: PCT/EP2014/073674
§ 371 (c)(1),
(2) Date: May 19, 2016

(87) PCT Pub. No.: WO2015/074864
PCT Pub. Date: May 28, 2015

(65) Prior Publication Data
US 2016/0297727 A1    Oct. 13, 2016

(30) Foreign Application Priority Data
Nov. 20, 2013  (EP) .................................... 13193626

(51) Int. Cl.
*C01B 3/38* (2006.01)
*C07C 2/80* (2006.01)
(Continued)

(52) U.S. Cl.
CPC .................. *C07C 2/80* (2013.01); *C01B 3/38* (2013.01); *H01M 8/04097* (2013.01);
(Continued)

(58) Field of Classification Search
CPC . C07C 2/80; H01M 8/04; H01M 8/06; H01M 8/0606; H01M 8/0612;
(Continued)

(56) References Cited

U.S. PATENT DOCUMENTS 2,080,930 A    5/1937   Rose
4,350,835 A    9/1982   Chester et al.
(Continued)

FOREIGN PATENT DOCUMENTS

WO    WO 2013/048705 A1    4/2013
WO    WO-2013082110 A1 *   6/2013    ........... B01D 71/024

OTHER PUBLICATIONS

A. Stambouli et al., "Solid oxide fuel cells (SOFCs): a review of an environmentally clean and efficient source of energy," Renewable and Sustainable Energy Review, New York, NY, US, vol. 6, No. 5, Oct. 1, 2002, pp. 433-455.
(Continued)

*Primary Examiner* — James Lee
(74) *Attorney, Agent, or Firm* — Blank Rome LLP

(57) ABSTRACT

A fuel cell reactor, preferably a solid oxide fuel cell (SOFC) reactor, for performing direct conversion of a hydrocarbon-containing gas to a higher hydrocarbons product is confined by walls, where reactants are flown in the anode compartments and air is introduced to the cathode compartments, and where oxygen is transferred from one side of the walls to the other side to promote or inhibit a chemical reaction. The process for direct conversion of a hydrocarbon-containing gas to a higher hydrocarbons product takes place in the anode compartment of the reactor, in which produced hydrogen, limiting the conversion to the equilibrium, is reacted in situ with oxygen ions transferred from the cathode compartment to produce steam, thereby removing the equilibrium-limiting hydrogen from the reaction.

16 Claims, 7 Drawing Sheets

(51) Int. Cl.
  *H01M 8/0606* (2016.01)
  *H01M 8/0612* (2016.01)
  *H01M 8/0637* (2016.01)
  *H01M 8/0662* (2016.01)
  *H01M 8/04089* (2016.01)
  *H01M 8/12* (2016.01)
  *H01M 8/124* (2016.01)

(52) U.S. Cl.
  CPC ....... *H01M 8/0606* (2013.01); *H01M 8/0612* (2013.01); *H01M 8/0637* (2013.01); *H01M 8/0662* (2013.01); *H01M 8/0675* (2013.01); *H01M 8/12* (2013.01); *C01B 2203/0233* (2013.01); *C01B 2203/0405* (2013.01); *C01B 2203/048* (2013.01); *C01B 2203/0475* (2013.01); *C01B 2203/0495* (2013.01); *C01B 2203/066* (2013.01); *C01B 2203/127* (2013.01); *C01B 2203/1241* (2013.01); *C01B 2203/146* (2013.01); *C01B 2203/148* (2013.01); *H01M 2008/1293* (2013.01); *Y02E 60/50* (2013.01)

(58) Field of Classification Search
  CPC ............. H01M 8/0637; H01M 8/0662; H01M 8/04097; H01M 8/0675; H01M 8/12; C01B 3/38
  See application file for complete search history.

(56) References Cited

U.S. PATENT DOCUMENTS

| | | |
|---|---|---|
| 4,642,403 A | 2/1987 | Hyde et al. |
| 6,552,243 B2 | 4/2003 | Allison et al. |
| 7,968,759 B2 | 6/2011 | Iaccino et al. |
| 2011/0303550 A1 | 12/2011 | Coelho Tsou et al. |
| 2014/0275679 A1* | 9/2014 | Sofranko ............. B01D 71/024 585/310 |

OTHER PUBLICATIONS

Wikipedia definition of Fuel Cell: https://en.wikipedia.org/wiki/Fuel_cell.

* cited by examiner

FUEL CELL REACTOR AND A PROCESS FOR DIRECT CONVERSION OF A HYDROCARBON-CONTAINING GAS TO A HIGHER HYDROCARBONS PRODUCT

The present invention relates to a novel fuel cell reactor and a novel process for direct conversion of a hydrocarbon-containing gas to a higher hydrocarbons product, said process taking place in the anode compartment of the reactor.

In a preferred embodiment, the invention concerns a novel process for direct conversion of natural gas to aromatic compounds, especially monocyclic aromatics.

Higher hydrocarbons products, especially aromatic hydrocarbons such as benzene, toluene, ethylbenzene, styrene, xylenes and naphthalene, constitute important intermediates in the chemical industry, and the demand for these products continues to rise. In general, they are obtained by catalytic reforming from naphtha, which is in turn obtained from mineral oil. Recent studies have shown that global mineral oil reservoirs are more limited compared to the natural gas reservoirs. Therefore, the preparation of aromatic hydrocarbons from reactants which can be obtained from a hydrocarbon-containing gas, such as natural gas, is an alternative which is now also of economic interest. The main component of natural gas is typically methane.

A process as outlined on the block diagram in FIG. 1 is being investigated by many research institutes and research centres. In this process, natural gas or methane is converted into aromatic compounds, especially benzene, in a conventional reactor. Heat may be supplied to the reaction zone. The effluent consisting of product(s) and unconverted reaction precursors is separated in a separation unit, where condensable products, such as benzene, are condensed out and non-condensable compounds are recycled back to the reactor after hydrogen has been partly or completely removed therefrom.

An alternative to the above-mentioned process is the in situ removal of hydrogen from the reactor as shown in FIG. 2. A high temperature membrane is used for selective and continuous separation of hydrogen from the reactor. This will boost the aromatics production by shifting the equilibrium reaction

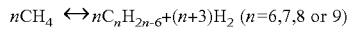

$$nCH_4 \leftrightarrow nC_nH_{2n-6} + (n+3)H_2 \ (n=6,7,8 \text{ or } 9)$$

to the right. In both processes, a catalyst being either W or Ru~Mo over HZSM5 is used to convert methane to benzene. Hydrogen is the by-product of this equilibrium reaction which limits the methane conversion thermodynamically.

A number of processes for converting methane to aromatic hydrocarbons are known. Thus, U.S. Pat. No. 7,968,759 describes a process for production of aromatics from methane, in which a feed containing methane is supplied to one or more reaction zones containing a catalytic material, operating under reaction conditions effective to convert at least a portion of the methane to aromatic hydrocarbons. The reaction zone(s) is/are operated with an inverse temperature profile.

U.S. Pat. No. 4,642,403 discloses a process for producing aromatic hydrocarbons, said process comprising bringing a hydrocarbon feedstock containing at least 10% by weight C2 hydrocarbons, preferably at least 50% by weight C2 hydrocarbons, into contact with a catalyst composition in the vapour phase at a temperature from 500 to 750° C. Said catalyst composition comprises (i) an aluminosilicate loaded with gallium as a gallium compound and/or as gallium ions and having a silica-to-alumina molar ratio of at least 5:1, and (ii) a Group VIII metal selected from rhodium and platinum. The aluminosilicate loaded with gallium is preferably an MFI or an MEL type zeolite.

From U.S. Pat. No. 4,350,835 it is known that ethane can be converted to aromatics over a gallium-activated zeolite. More specifically, a catalytic process is provided for converting gaseous feedstocks containing ethane to liquid aromatics by contacting said gaseous feeds in the absence of added air or oxygen, under conversion conditions, with a crystalline zeolite catalyst having incorporated therein a minor amount of gallium, thereby converting the ethane in the feedstock to aromatics and recovering a liquid mixture of benzene, toluene and xylene. The crystalline zeolite is selected from the group consisting of ZSM-5, ZSM-11, ZSM-12, ZSM-35, and ZSM-38, and the zeolite is preferably an acid form.

According to U.S. Pat. No. 6,552,243, a molybdenum-loaded crystalline aluminosilicate molecular sieve that exhibits the MFI crystal structure and has a silica-to-alumina ratio of about 50:1 is useful for aromatizing a hydrocarbon feed stream. The crystalline aluminosilicate preferably has an external surface acidity selectively passivated by means of an amorphous silica layer. A process for the aromatization of methane comprises a one-step or multi-step process in which a feed stream comprising at least methane is contacted with a catalyst composition comprising the preferred molecular sieve, at hydrocarbon conversion conditions that include a temperature of 600-800° C., an absolute pressure of less than 5 atmospheres and a Weight Hourly Space Velocity (WHSV) of $0.1^{-10} \ h^{-1}$, with the external surface acidity of the crystalline aluminosilicate preferably selectively passivated by an amorphous silica layer. C6+ aromatic hydrocarbons are preferably recovered from the process by means of an intermediate separation step.

Finally, US 2011/0303550 describes a process for converting aliphatic hydrocarbons having 1 to 4 carbon atoms to aromatic hydrocarbons, comprising the steps of: a) converting a reactant stream which comprises at least one aliphatic hydrocarbon having 1 to 4 carbon atoms in the presence of a catalyst under non-oxidative conditions to a product stream comprising aromatic hydrocarbons and hydrogen, and b) electrochemically removing at least some of the hydrogen formed in the conversion from the product stream by means of a gas-tight membrane-electrode assembly which has at least one selectively proton-conducting membrane and, on each side of the membrane, at least one electrode catalyst. At least some of the hydrogen is oxidized to protons over the anode catalyst on the retentate side of the membrane, and the protons, after passing through the membrane, on the permeate side over the cathode catalyst, are partly reduced to hydrogen with application of a voltage, and partly reacted with oxygen to give water to generate electrical power, the oxygen originating from an oxygen-comprising stream which is contacted with the permeate side of the membrane.

DETAILED DESCRIPTION OF THE INVENTION

Figure 1:
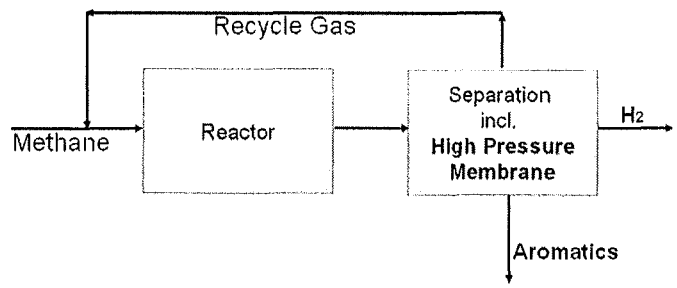
FIG. 1 is a block diagram of a prior art process for converting natural gas or methane into aromatic compounds, especially benzene, in a conventional reactor.
Figure 2:
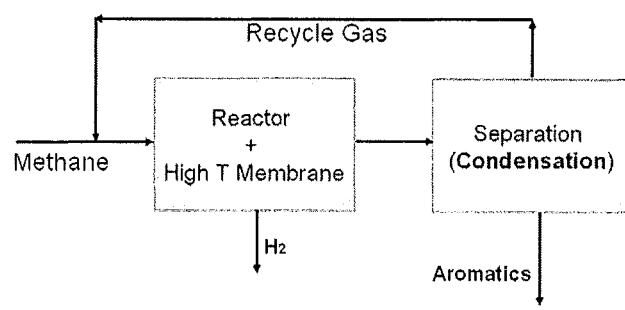
FIG. 2 is a block diagram of an alternative to the process of FIG. 1, involving the in situ removal of hydrogen from the reactor.

One possible reaction route for obtaining aromatics from aliphatics is that of non-oxidative dehydroaromatization (DHAM). The reaction is effected here under non-oxidative conditions, especially with exclusion of oxygen. In DHAM, a dehydrogenation and cyclization of the aliphatics to give the corresponding aromatics with release of hydrogen takes place. This way 1 mol of benzene and 9 mol of hydrogen are formed from 6 mol of methane.

The present invention is based on this reaction route. More specifically, methane is converted to benzene and/or other aromatics according to the equilibrium reaction

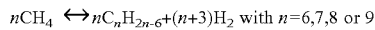

$nCH_4 \leftrightarrow nC_nH_{2n-6} + (n+3)H_2$ with $n=6,7,8$ or $9$ where hydrogen is reacted in situ with oxygen ions transferred from the cathode department to produce steam.

Both the present invention and the above-mentioned US 2011/0303550 are dealing with a process for production of higher hydrocarbons from methane or from light hydrocarbon gases by overcoming the thermodynamic equilibrium barrier to enhance conversion. This is done by taking out hydrogen by-product. However, fundamental differences exist between the present invention and US 2011/0303550. The latter removes hydrogen from the reaction chamber by oxidizing hydrogen atoms to protons and transferring these out of the reactor through a proton (f) membrane. In the process according to the present invention, hydrogen is oxidized inside the reaction chamber by reacting with oxygen ions which are brought into the reaction chamber via an oxygen ion membrane.

In US 2011/0303550, electric power is applied onto the membrane to transfer $H^+$ ions out of the reaction chamber, whereas in the process of the invention, electric power is produced from the membrane.

Furthermore, in US 2011/0303550, hydrogen is reacted with oxygen in the cathode compartment removed from the reaction chamber, whereas in the process of the invention, water is produced inside the reaction chamber by reaction of oxygen with hydrogen on the anode surface. As a result of these differences, the total H/C ratio declines during the reaction in US 2011/0303550, while in the process of the invention, the total H/C ratio is constant.

More specifically, the present invention concerns a fuel cell reactor for performing direct conversion of a hydrocarbon-containing gas to a higher hydrocarbons product, said fuel cell reactor being confined by walls, where reactants are flown in the anode compartments and air is introduced to the cathode compartments, and where oxygen is transferred from one side of the walls to the other side to promote or inhibit a chemical reaction. Furthermore it concerns a process for direct conversion of a hydrocarbon-containing gas to a higher hydrocarbons product in the anode compartment of a fuel cell reactor, in which produced hydrogen, limiting the conversion to the equilibrium, is either removed or reacted in situ with oxygen ions transferred from the cathode compartment to produce steam, thereby removing the equilibrium-limiting hydrogen from the reaction.

Preferably the fuel cell reactor is a solid oxide fuel cell (SOFC) reactor.

The hydrocarbon-containing gas can be any gas containing methane, such as natural gas, biogas, synthetic natural gas or shale gas. Preferably it is natural gas.

The higher hydrocarbons product is either a gaseous or a liquid product.

The methane-containing gas is preferably cleaned from impurities such as sulfur, nitrogen and any non-hydrocarbon species. The cleaned gas may be further treated to remove or convert any hydrocarbonic species except methane in order to produce a methane-rich feed gas for the solid oxide fuel cell reactor.

The hydrocarbon treating unit is preferably a pre-reformer operating in an optimized condition to convert higher hydrocarbons, i.e. C2+, with steam to hydrogen and carbon oxides.

Methane-rich gas is converted to aromatic products according to the equilibrium reaction

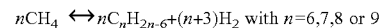

$nCH_4 \leftrightarrow nC_nH_{2n-6} + (n+3)H_2$ with $n=6,7,8$ or $9$ where hydrogen is reacted in situ with oxygen ions transferred from the cathode compartment to produce steam.

Preferably the unconverted feed gas in the fuel cell reactor is separated and recycled back to the reactor.

A conversion catalyst can be coated on the anode surface, loaded in the anode compartment or a combination of both.

A fraction of the gas from the fuel cell reactor effluent, which contains hydrogen, may be used to clean and treat the raw hydrocarbon feed gas.

Figure 3:
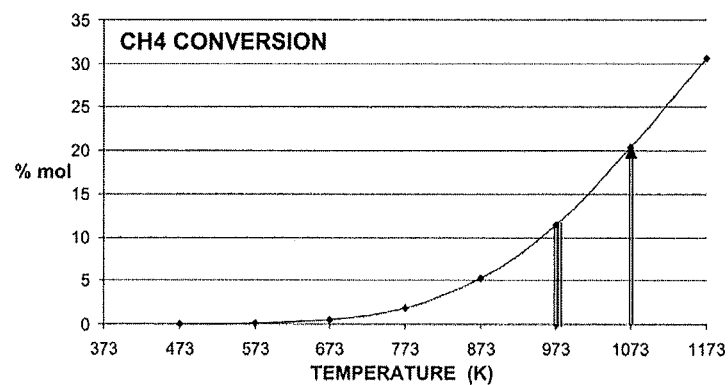
FIG. 3 is a graph showing the equilibrium conversion of methane in mol % versus temperature.

The equilibrium conversion of methane ($CH_4$) in mol % versus temperature is shown graphically in FIG. 3. From the graph it is seen that the conversion is limited to a maximum of about 20% in a practical operating temperature range below 1073 K (800° C.)

Figure 4:
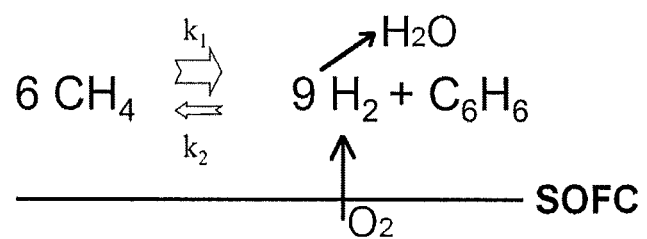
FIG. 4 shows a process in which the conversion of methane to benzene is enhanced beyond the thermodynamic equilibrium limit by employing a planar or tubular fuel cell reactor, in which the produced hydrogen is consumed to generate steam and electricity.

It has surprisingly turned out that the conversion of methane to benzene can be enhanced beyond the thermodynamic equilibrium limit by employing a planar or tubular fuel cell reactor, in which the produced hydrogen is consumed to generate steam and electricity; see FIG. 4.

The SOFC reactor, which is preferred for this purpose, is a special kind of SOFC in which anode activity is not needed. For this reason the anode active layer can be eliminated, leaving only the cathode, an electrolyte and possibly anode support layers.

More specifically, the reactor for performing the process according to the invention is a reactor confined by fuel cell walls, where reactants are flown in the anode compartments and air is introduced to the cathode compartments, and wherein oxygen is transferred from one side of the walls to the other side to promote or inhibit a chemical reaction. Said chemical reaction is preferably a heterogeneous catalytic gas phase reaction.

In the reactor according to the invention, the fuel cell walls are solid oxide fuel cell walls of any type operating at elevated temperatures, and where the catalytic chemical reaction is carried out on the anode side of the cell, resulting in oxygen ions being transferred from the cathode side (the air side) and reacted with hydrogen on the anode side (the fuel side).

Oxygen from the cathode side is ionized and diffused through the electrolyte. On the anode side, where the conversion of methane to benzene takes place, hydrogen (formed as a by-product) reacts with oxygen to form steam. Electrons released from the anode surface are conveyed to the cathode surface via a closed circuit.

When using SOFC reactors for the purpose of the invention, the reaction chamber can be designed in two possible ways:

(1) When the SOFC is used as catalyst, the methane-to-aromatics catalyst is deposited on the anode surface. The reaction takes place on the anode surface, where hydrogen is continuously consumed.

(2) When the SOFC is used as reactor wall, the methane-to-aromatics catalyst in pellet or monolith form is filled in a reactor with SOFC walls. Then the produced hydrogen will be converted to steam on the reactor walls.

A combination of designs (1) and (2) is also possible.

Figure 5:
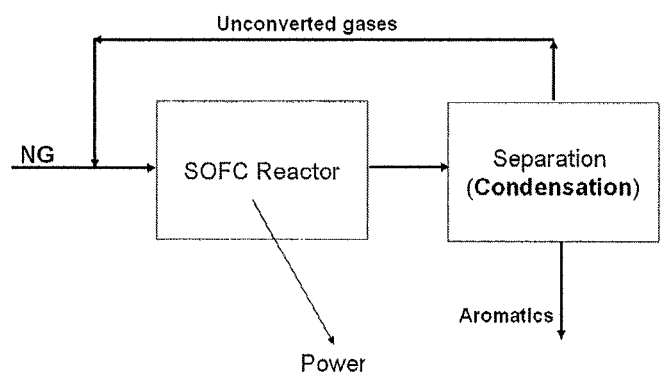
FIG. 5 is a block diagram showing the schematic layout of the process according to the present invention.

The schematic layout of the process according to the invention is shown in the block diagram of FIG. 5. The SOFC reactor produces aromatics and steam. Hydrogen is consumed to generate power. Air with a temperature of 700-800° C. is supplied to the cathode side of the SOFC wall. The separation unit can e.g. be a condensation unit. Water and aromatics are separated in a liquid settling vessel. Unconverted methane gas and hydrogen is compressed and recycled back to the reactor inlet.

Figure 6A:
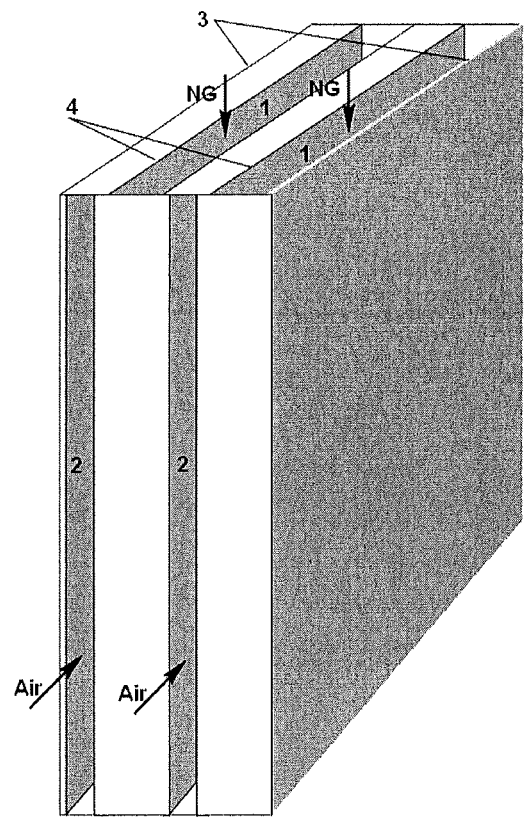
FIG. 6a is a schematic drawing illustrating one possible SOFC reactor structure.

FIG. 6a is a schematic drawing illustrating one possible SOFC reactor structure. For the sake of simplicity a two-channel reactor is shown. Natural gas is passed through the channels 1. These channels are loaded with a suitable catalyst for converting methane to aromatics. The reaction channels are confined between the anode surfaces of the SOFC (4) and the metal interconnects (3). An intertwined metal network is inserted between two surfaces, allowing current flow across the channels.

Air is blown to the channels (2). These channels are confined between the cathode surfaces of the SOFC (4) and the metal interconnects (3). A suitable interconnect network may also be provided here to pass the current flow. Alternatively, corrugated plates can be used as metal interconnects.

Figure 6B:
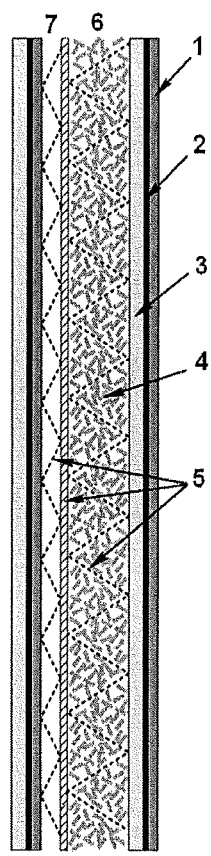
FIG. 6b shows a top view of a possible arrangement for one module of the SOFC reactor structure.

FIG. 6b shows a top view of a possible arrangement for one module of the SOFC reactor. One reactor module is confined between two SOFCs each consisting of a cathode layer (1), an electrolyte layer (2) and an anode layer (3). Catalyst pellets (4) are loaded in the anode compartment (6). Air is flown through the cathode compartment (7). Two compartments are separated by an electrically conductive interconnect (5).

Current is collected from both ends of the reactor.

The process according to the invention presents a number of advantages over the known processes. These advantages are as follows:

steam generation in the reactor will potentially suppress or inhibit carbon deposition;
a high methane conversion is obtained by shifting the reaction towards aromatics production;
a high hydrogen removal rate compared to high temperature membranes is obtained;
a simple/cheap aromatics separation unit can be used;
the hydrogen/oxygen reaction heat and the ohmic loss heat are supplied to the endothermic aromatics synthesis reaction, and electricity is generated.

The invention is illustrated further by the following examples.

Example 1

Figure 7:
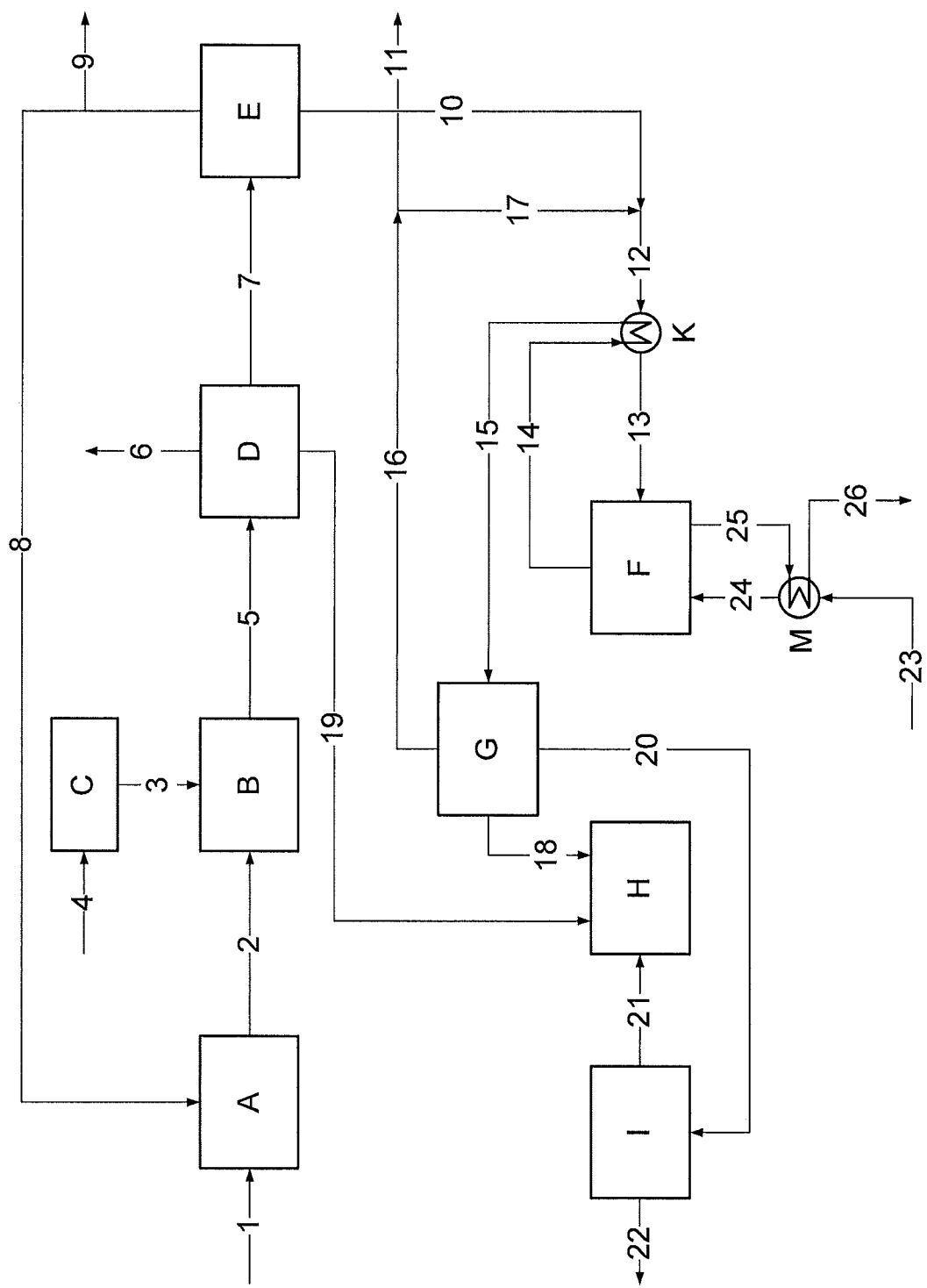
FIG. 7 is a process layout of the invention as described in Example 1.

Referring to FIG. 7, natural gas (NG) is desulfurized in the NG HDS (hydrodesulfurization) unit A and fed to the pre-reforming unit B, which operates at a relatively low temperature, along with enough steam from the steam generation unit C to merely reform higher hydrocarbons. The prereformed natural gas is devoid of any higher hydrocarbons and almost devoid of carbon monoxide. The effluent from the pre-reformer is cooled in the $CO_2$/water separation unit D to condense out the water. The content of carbon dioxide in the dry gas is also removed in this unit. Part of the hydrogen from the pre-reformed gas is separated in the membrane unit E and recycled back to the NG HDS unit A. Dry methane-rich gas from the membrane unit mixed with recycle gas from the SOFC reactor F is heated up to the reaction temperature by means of heat exchanger K and fed to the SOFC reactor, and hot air is blown through the cathode channels of the SOFC reactor. The product gas from the anode channels is cooled down using the reactor feed gas and then led to the phase separation unit G, where organic, aqueous and gaseous phases are separated. A small fraction of the gaseous phase is purged to prevent accumulation of inert gases in the synthesis loop, and the rest of the gas is cleaned up and recycled back to the SOFC reactor. The organic phase is sent to the distillation unit I for further purification of the final product. The aqueous phase is sent to the waste water treatment unit H.

NG is supplied to the plant at a pressure of 30 barg.

The NG HDS unit A is operated under the following operating conditions: Temperature 350° C.; pressure 30 barg; hydrogen-to-feed gas ratio 0.04 (mol/mol); NG composition (mol %): 90% methane, 4% ethane, 2% propane; 4% inert; required heat 0.79 MW.

The pre-reforming unit B is operated under the following operating conditions: Temperature 350° C.; pressure 29 barg; steam-to-carbon (S/C) ratio 0.6 (mol/mol); steam consumption 5.1 MTPD; heat removal 2.48 MW assuming superheated steam inlet at 350° C. The reactor is adiabatic.

The $CO_2$/water separation unit D is operated under the following operating conditions: Temperature 40° C.; pressure 27 barg; water condention temperature 60° C. (air cooler can be used); carbon dioxide removal yield over 99%; carbon dioxide inlet concentration 1.8 mol %.

The membrane unit E, which is an optional unit, is operated under the following operating conditions: Temperature 40° C.; pressure 25 barg; hydrogen molar recovery 84%; methane molar slip 9%; recycle hydrogen gas compressor power 44 kW.

The SOFC reactor F has the following technical data: Module (cell) dimension 1×2×0.05 m; number of cells 1080; catalyst W on HZSM-5 with a particle size of 1 mm; catalyst volume 10.8 $m^3$; air blower power 786 kW; net electrical power output 3.3 MW (5% ohmic and DC/AC converter loss); pressure drop 0.9 bar.

The reactor is operated under the following operating conditions: Temperature 800° C. (average); pressure 0.2 barg in the cathode side (air) and 1.1 barg in the anode side (process gas); air utilization 5.5%; current density 2000 $A/m^2$; gas hourly space velocity (GHSV) 1000 $h^{-1}$; process gas recycle ratio 9.6; recycle gas compressor power 1612 kW; air flow rate 10377 $Nm^3$/h.

The methane conversion is 5.75% compared to 0.57% conversion in a packed bed at the same process condition. The hydrogen consumption rate is 2379 Nm³/h equal to a water production rate of 1912 kg/h. Hot air exhaust from heat exchanger M is available at 95° C. for utility water heating. The generated heat amounts to 72.45 MW without considering ohmic loss.

The phase separation unit is operated under the following operating conditions: Temperature 40° C.; atmospheric pressure; required heat removal 1.86 MW.

The material balance values for the process layout of this example are given in Table 1.

Example 2

Figure 8:
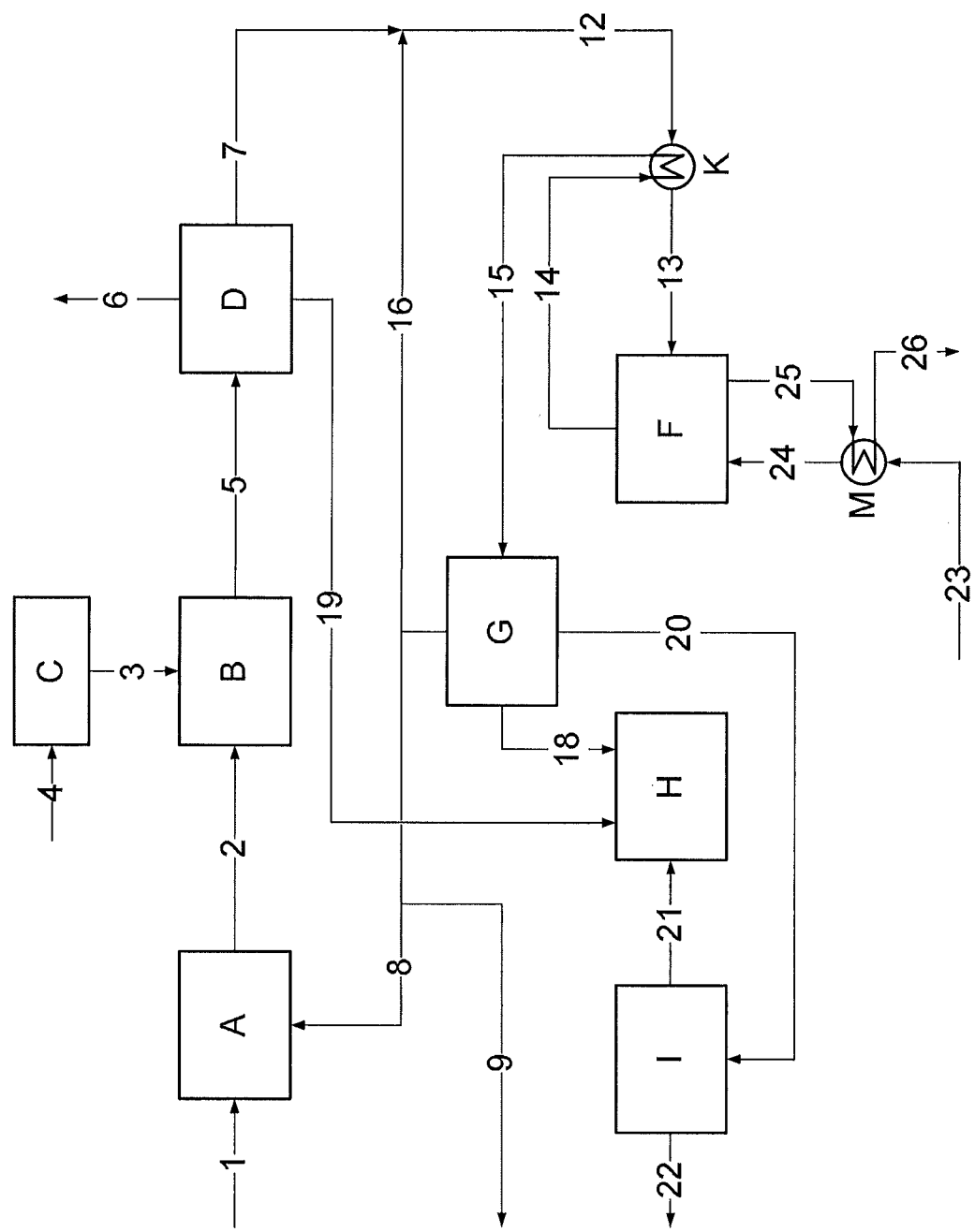
FIG. 8 is an alternative of the process layout of FIG. 7, in which the membrane unit is eliminated.

An alternative to the process layout, which is shown in FIG. 7 and described in Example 1, is shown in FIG. 8. This alternative layout differs from the above layout in that the membrane unit is eliminated. In this case the hydrogen required for the NG HDS (hydrodesulfurization) unit is obtained from the effluent stream from the SOFC reactor.

Example 3

An alternative to the process layout described in Example 2 and shown in FIG. 8 is a layout without water and carbon dioxide removal unit. In this layout, the SOFC feed gas is supplied directly from the pre-reforming unit at the pre-reformer outlet temperature.

reaction and reacts in situ with hydrogen on the anode side of the cell, thereby removing equilibrium-limiting hydrogen from the reaction and maintaining a constant total hydrogen to carbon ratio in the anode side of the cell, wherein the anode side of the cell does not comprise an anode active layer.

2. The reactor according to claim 1, where the chemical reaction is a heterogeneous catalytic gas phase reaction.

3. The reactor according to claim 1, where hydrogen is generated as a by-product in the chemical reaction, which limits conversion to the equilibrium.

4. The reactor according to claim 1, where the fuel cell walls are solid oxide fuel cell walls of any type operating at elevated temperatures, and where the chemical reaction is a catalytic chemical reaction and is carried out on the anode side of the cell, resulting in oxygen ions being transferred from the cathode side of the cell and reacted with hydrogen on the anode side of the cell.

5. The reactor according to claim 4, wherein oxygen ions transferred via an electrolyte from the cathode side of the cell are reacted in situ with hydrogen on the anode side of the cell, thereby producing $H_2O$ and removing hydrogen from the chemical reaction.

6. The reactor according to claim 1, wherein the fuel cell reactor further comprises a high temperature membrane configured to selectively and continuously separate hydrogen from the fuel cell reactor.

7. A process for direct conversion of a hydrocarbon-containing gas to a higher hydrocarbons product in the anode compartments of a fuel cell reactor according to claim 1, in which produced hydrogen, limiting the conversion to the equilibrium, is reacted in situ with oxygen ions transferred from the cathode compartments to produce steam, thereby removing the equilibrium-limiting hydrogen from the reaction.

8. The process according to claim 7, wherein the hydrocarbon-containing gas is any methane-containing gas.

9. The process according to claim 7, wherein the higher hydrocarbons product is a gaseous or a liquid product.

TABLE 1

Material balance values for Example 1 (see FIG. 7 for stream numbers)

| | Stream No. | | | | | | | | | | | | | |
|---|---|---|---|---|---|---|---|---|---|---|---|---|---|---|
| | 1 | 2 | 8 | 5 | 7 | 10 | 17 | 13 | 15 | 20 | 9 | 11 | 23 | 26 |
| Name | NG | MPS | Rec. $H_2$ | Syngas | $CO_2$-free syngas | $CH_4$-rich Makeup gas | Rec. gas | Feed gas | Effluent gas | Product | H2 purge | Purge gas | Air feed | Exhaust Air |
| mol % | | | | | | | | | | | | | | |
| $N_2$ | 4.0 | 0.0 | 2.7 | 2.3 | 3.6 | 3.7 | 5.5 | 5.3 | 5.2 | 0.0 | 2.7 | 5.5 | 79.0 | 79.9 |
| $O_2$ | 0.0 | 0.0 | 0.0 | 0.0 | 0.0 | 0.0 | 0.0 | 0.0 | 0.0 | 0.0 | 0.0 | 0.0 | 21.0 | 20.1 |
| $H_2$ | 0.0 | 0.0 | 30.7 | 3.0 | 4.6 | 0.8 | 31.6 | 29.4 | 30.1 | 0.0 | 30.7 | 31.6 | 0.0 | 0.0 |
| $CH_4$ | 90.0 | 0.0 | 66.6 | 59.5 | 91.8 | 95.5 | 62.9 | 65.3 | 60.0 | 0.0 | 66.6 | 62.9 | 0.0 | 0.0 |
| $C_2H_6$ | 4.0 | 0.0 | 0.0 | 0.0 | 0.0 | 0.0 | 0.0 | 0.0 | 0.0 | 0.0 | 0.0 | 0.0 | 0.0 | 0.0 |
| $C_3H_8$ | 2.0 | 0.0 | 0.0 | 0.0 | 0.0 | 0.0 | 0.0 | 0.0 | 0.0 | 0.0 | 0.0 | 0.0 | 0.0 | 0.0 |
| CO | 0.0 | 0.0 | 0.0 | 0.0 | 0.0 | 0.0 | 0.0 | 0.0 | 0.0 | 0.0 | 0.0 | 0.0 | 0.0 | 0.0 |
| $CO_2$ | 0.0 | 0.0 | 0.0 | 1.2 | 0.0 | 0.0 | 0.0 | 0.0 | 0.0 | 0.0 | 0.0 | 0.0 | 0.0 | 0.0 |
| $C_6H_6$ | 0.0 | 0.0 | 0.0 | 0.0 | 0.0 | 0.0 | 0.0 | 0.0 | 0.6 | 100.0 | 0.0 | 0.0 | 0.0 | 0.0 |
| $H_2O$ | 0.0 | 100.0 | 0.0 | 34.0 | 0.0 | 0.0 | 0.0 | 0.0 | 4.1 | 0.0 | 0.0 | 0.0 | 0.0 | 0.0 |
| T (° C.) | 21 | 350 | 90 | 60 | 60 | 40 | 100 | 800 | 113 | 40 | 40 | 40 | 25 | 95 |
| P (barg) | 30.0 | 30.0 | 30.0 | 27.5 | 25.5 | 3.5 | 1.3 | 1.1 | 0.1 | 0.1 | 5.0 | 0.1 | 0.0 | 0.1 |
| Flow (kmol/h) | 172 | 118 | 26 | 324 | 210 | 183 | 2376 | 2559 | 2623 | 16 | 0.7 | 125 | 4686 | 4633 |
| MW (kg/kmol) | 17.64 | 18.01 | 12.09 | 16.91 | 15.83 | 16.37 | 12.28 | 12.57 | 12.91 | 78.13 | 11.43 | 12.27 | 28.85 | 28.81 |
| Density (kg/m³) | 23.45 | 11.05 | 12.42 | | 15.50 | 2.85 | 0.914 | 0.30 | | 856.23 | 2.79 | 0.52 | 1.18 | 1.05 |

The invention claimed is:

1. A fuel cell reactor for performing direct conversion of a hydrocarbon-containing gas to a higher hydrocarbons product, said fuel cell reactor being confined by walls, where reactants are flown in anode compartments and air is introduced to cathode compartments, the anode compartments comprising a respective anode side of the cell and the cathode compartments comprising a respective cathode side of the cell, and where oxygen is transferred from one side of the walls to another side to promote or inhibit a chemical 10. The process according to claim 7, wherein methane is converted to monocylic aromatics according to the equilibrium reaction:

$$nCH_4 \leftrightarrow nC_nH_{2n-6} + (n+3)H_2 \; (n=6,7,8 \text{ or } 9)$$

where hydrogen is reacted in situ with oxygen ions transferred from the cathode compartments to produce steam in the fuel cell reactor.

11. The process according to claim 10, wherein the fuel cell reactor is a solid oxide fuel cell reactor.

12. The process according to claim 8, wherein the methane-containing gas is cleaned from impurities such as sulfur, nitrogen and any non hydrocarbon species.

13. The process according to claim 12, wherein the cleaned gas is further treated to remove or convert any hydrocarbon species except methane in order to produce a methane-rich feed gas for the fuel cell reactor.

14. The process according to claim 12, wherein a pre-reformer operating in an optimized condition is used to convert higher hydrocarbons with steam to hydrogen and carbon oxides.

15. The process according to claim 14, wherein unconverted feed gas in the fuel cell reactor is separated and recycled back to the reactor.

16. The process according to claim 15, wherein a fraction of effluent gas from the fuel cell reactor, which contains hydrogen, is used to clean and treat feed gas for the reactor.

* * * * *